United States Patent [19]

Yoshioka et al.

[11] Patent Number: 4,839,767

[45] Date of Patent: Jun. 13, 1989

[54] ELEMENT AND DEVICE FOR DETECTING INTERNAL FAULTS IN AN INSULATING GAS CHARGED ELECTRICAL APPARATUS

[75] Inventors: Takeo Yoshioka; Tadao Minagawa; Toshihiro Suzuki; Ichiro Yamasaki; Yoshifumi Matsushita, all of Amagasaki, Japan

[73] Assignee: Mitsubishi Denki Kabushiki Kaisha, Japan

[21] Appl. No.: 149,168

[22] Filed: Jan. 27, 1988

[30] Foreign Application Priority Data

| Feb. 2, 1987 | [JP] | Japan | 62-12842[U] |
| Apr. 17, 1987 | [JP] | Japan | 62-93286 |
| Jun. 30, 1987 | [JP] | Japan | 62-160838 |
| Jul. 3, 1987 | [JP] | Japan | 62-165408 |

[51] Int. Cl.⁴ ............... H02H 5/00; G01N 27/12
[52] U.S. Cl. ................................ 361/42; 73/23; 73/27 R; 338/34; 340/634; 361/1; 422/98
[58] Field of Search ........... 361/1, 14, 42, 111, 361/115, 117, 120; 73/1 G, 23, 27 R, 19; 340/634; 200/144 R, 148 R; 422/88, 90, 98; 338/34

[56] References Cited

U.S. PATENT DOCUMENTS

| 3,648,110 | 3/1972 | Knight | 361/111 X |
| 3,970,431 | 7/1976 | Wise | 23/232 E |
| 4,046,512 | 9/1977 | Kaczmarek et al. | 23/253 |
| 4,092,119 | 5/1978 | Baier et al. | 23/253 TP |
| 4,170,770 | 10/1979 | Ichinose et al. | 340/634 |
| 4,259,292 | 3/1981 | Ichinose et al. | 422/98 |
| 4,271,124 | 6/1981 | Speeter | 422/68 |
| 4,324,761 | 4/1982 | Harris | 422/97 |
| 4,394,635 | 7/1983 | Foss | 336/55 |
| 4,436,699 | 3/1984 | Narato et al. | 422/68 |
| 4,457,161 | 7/1984 | Iwanaga et al. | 73/23 |
| 4,481,499 | 11/1984 | Arima et al. | 338/34 |
| 4,505,146 | 3/1985 | Miners | 73/19 |
| 4,509,034 | 4/1985 | Sakai | 338/34 |
| 4,534,099 | 8/1985 | Howe | 29/527 |
| 4,555,930 | 12/1985 | Leach et al. | 73/23 |
| 4,661,320 | 4/1987 | Ito et al. | 422/86 |
| 4,685,018 | 8/1987 | Tada et al. | 361/1 |
| 4,685,325 | 8/1987 | Warchol | 73/19 |
| 4,688,136 | 8/1987 | Yamauchi | 361/120 |
| 4,704,607 | 11/1987 | Teather et al. | 73/1 G X |
| 4,709,291 | 11/1987 | Eggert et al. | 361/2 |
| 4,723,439 | 2/1988 | Asakura et al. | 73/29 |

OTHER PUBLICATIONS

"R&D Status Report Electrical Systems Division", EPRI Journal, Mar. 1982, pp. 42–46.
Van Nostrand's Scientific Encyclopedia Fifth Edition "Thermoelectric Cooling".
EPRI report, Oct. 1982.

Primary Examiner—A. D. Pellinen
Assistant Examiner—David A. Osborn
Attorney, Agent, or Firm—Leydig, Voit & Mayer

[57] ABSTRACT

An element for detecting internal faults in an insulating gas charged electrical apparatus comprises a substrate disposed in the electrical apparatus charged with an insulating gas, a pair of electrodes disposed on the substrate, and a thin metal film covering the pair of electrodes and the exposed surface of the substrate. This film is capable of producing fluorides with low conductivity upon reacting with a decomposed gas produced by internal faults of the electrical apparatus. Since the thin metal film exhibits high response characteristics readily in reaction with even a trace amount of a decomposed gas, it is possible to promptly detect faults occurring in the electrical apparatus, such as a partial discharge or local heating. In addition, a device for detecting internal faults in an insulating gas charge electrical apparatus using the internal fault detection element utilizes an optical signal for transmitting signals. Accordingly, the device is free from electromagnetically induced interference and is capable of remote monitoring because of the low level of loss in signal transmission.

26 Claims, 15 Drawing Sheets

ELEMENT AND DEVICE FOR DETECTING INTERNAL FAULTS IN AN INSULATING GAS CHARGED ELECTRICAL APPARATUS

BACKGROUND OF THE INVENTION

1. Field of the Invention

The present invention relates to an element and device for detecting internal faults in an electrical apparatus charged with an insulating gas. More particularly, the present invention relates to a device for detecting internal faults in an electrical apparatus charged with an insulating gas such as $SF_6$ gas, by using the fact that the presence of internal faults in the insulating gas charged electrical apparatus can be detected by the generation of decomposed $SF_6$ gas.

2. Statement of Related Art

FIG. 1 is a partial cross-sectional view illustrating a conventional internal fault detection device for an insulating gas charged electrical apparatus incorporating an internal fault element, as disclosed in, for instance, Japanese Patent Publication No. 57-38091. In FIG. 1, a hermetic grounded metal vessel 1 is provided in a part of an electrical apparatus (not shown) charged with an insulating gas such as $SF_6$, the hermetic grounded metal vessel 1 also being filled with $SF_6$ gas 2. A detection element supposing container 3 is provided substantially in the center of the hermetic grounded metal vessel 1. An internal fault detection element 4 constituted by a thin aluminum (Al) metal plate with a thickness of, for instance, about 5μm is supported inside the element supporting container 3 in an upper portion thereof. In addition, a substance 6 containing crystalized water such as $CuSO_4 \cdot 5H_4O$, which releases water upon coming into contact with a decomposed $SF_6$gas, is accommodated in a bottom portion of the element supporting container 3. A plurality of gas permeable holes 7 are provided on side surfaces of the element supporting container 3. In addition, external conductors 8 connected to an external circuit (not shown) are provided on the outside of the hermetic grounded metal vessel 1. Both ends of these external conductors 8 are electrically connected to the internal fault detection element 4 via insulated terminals 9 that pass air-tightly through a side wall portion of the hermetic grounded metal vessel 1 as well as via internal conductors 5 disposed inside the hermetic grounded metal vessel 1.

The conventional internal fault detection device is constructed as described above, and when a fault, such as a discharge, occurs in the hermetic grounded metal vessel 1, the $SF_6$2 is decomposed to produce an active fluorinated sulfur compound gas of $SF_4$, $SOF_2$, HF, etc., i.e., a decomposed $SF_6$ gas. This decomposed $SF_6$ gas enters the inside of the element supporting container 3 through the through holes 7 provided in the side surfaces thereof and is converted into HF upon reacting with a trace amount of water which is present in the $SF_6$ gas 2 in the container 3, and with water and the like which is released from the substance 6 containing crystallized water. The internal fault detection element 4 produces $AlF_3$ in a chemical reaction that takes place inside the container 3 which contains both the decomposed $SF_6$ gas and water. That reaction

$$Al + 3HF \rightarrow AlF_3 + 3/2 H_2$$

Thus, a part of the internal fault detection element 4 constituted by the conductive Al metal plate is converted into nonconductive $AlF_3$ so that the value of its resistance changes. Thus, by measuring the resistance change by an external circuit via the external conductors 8, the occurrence of any fault in the electrical apparatus can be detected.

In the internal fault detection device described above, since the internal fault detection element 4 is formed of an Al metal plate, the reaction will not proceed adequately unless a high-concentration of $SF_6$ gas is used. Therefore, fault detection is only possible in cases where a high-concentration of decomposed $SF_6$ gas is present, as in the case of a ground fault, but the detection speed is low. However, fault detection cannot be effected sufficiently in cases where the concentration of the decomposed $SF_6$ gas is low as in the case of a partial discharge or local heating. Further, there arises a problem in that a material which releases water upon coming into contact with the decomposed $SF_6$ gas, such as the crystallized water-containing substance 6, is required.

FIG. 2 is a cross-sectional view schematically illustrating another device for detecting internal faults in an insulating gas charged electrical apparatus which is disclosed in Japanese Utility Model Laid-Open 61-40657. In FIG. 2, a hermetic vessel 11 for an electrical apparatus charged with an insulating gas, such as $SF_6$ is provided with a movable contactor 12, a nozzle 13 provided such as to surround this movable contactor 12, a fixed contactor 14 into which the movable contactor 12 comes into contact and from which it moves away, a high-voltage conductor 16 connected to the fixed contactor 14, and a spacer 15 supporting the high-voltage conductor 16. The hermetic vessel 11 is filled with $SF_6$ gas 2. An opening 17a of the hermetic vessel 11 is provided with a flange cover 17, on which a decomposed $SF_6$ gas detection portion 19 having an internal fault detection element is provided. A signal from the decomposed gas detection portion 19 is supplied to an external circuit (not shown) by means of conductors 20. A gas pipe 21a for introducing the $SF_6$ gas 2 into the hermetic vessel 11 is connected to a side pipe 21b of the hermetic vessel 11 at a gas pipe jointing portion 21.

The decomposed $SF_6$ gas resulting from the generation of a discharge or local heating in a conducting contact portion inside the $SF_6$ gas charged electrical apparatus moves to the decomposed $SF_6$ gas detection portion 19 by means of convection and diffusion, and reacts with a sensitive material disposed on the decomposed $SF_6$ detection portion 19, thereby causing a change in the electrical properties thereof. A signal representing this change in electrical properties is transmitted via the conductor 20 to a signal processing section (not shown), which in turn issues an alarm indicating that a fault is present in the electrical apparatus.

When this decomposed $SF_6$ gas detection portion 19 is installed in an existing insulating gas charged electrical apparatus which is not provided with a decomposed $SF_6$ gas detection portion, additional machining must be carried out so that the decomposed $SF_6$ gas detection portion 19 can be installed on the flange cover 17.

That is, the decomposed $SF_6$ gas detection portion 19 is conventionally fixed to the inner side of the flange cover 17, as shown in FIG. 2. Accordingly, there have been problems in that the flange of an existing insulating gas charged electrical apparatus must be machined or modified during checkups or the like so as to allow the installation of the decomposed $SF_6$ gas detection portion 19.

In addition, since the entire processing of signals from the internal fault detection element of the conventional apparatus as shown in FIG. 1 or 2 is effected electrically, there has been other problems in that detection accuracy is low in environments where a high electromagnetic field exists.

SUMMARY OF THE INVENTION

Accordingly, an object of the present invention is to provide an internal fault detection element which exhibits outstanding response characteristics by issuing a quick response even to a low-concentration decomposed $SF_6$ gases, and which is capable of detecting at an early stage faults such as discharge, local heating, etc. occurring in an electrical apparatus, thereby solving the problems of the prior art.

Another object of the present invention is to provide an internal fault detecting device for use in an insulating gas charged electrical apparatus which allows a decomposed $SF_6$ gas detection portion to be readily installed without requiring any particular machining or modification of an existing insulating gas charged electrical apparatus.

Still another object of the present invention is to provide an internal fault detection device which comprises a photoelectric conversion section for converting a change in a current caused by a change in resistance of an internal fault detection element into an optical signal, and a signal processing section for processing the optical signal sent from the photoelectric conversion section via an optical fiber. This apparatus provides the advantages of high insulation, high pressure resistance, non-inductiveness, low loss, light weight, and safety that are peculiar to optical fibers, and makes it possible to effect remote monitoring safely at high speed and with high precision even in adverse environments where high electromagnetic fields or the like exist, for which remote monitoring has been difficult with a conventional apparatus.

In order to achieve the above objects, according to one aspect of the present invention, there is provided an element for detecting internal faults in an insulating gas charged electrical apparatus comprising: a substrate formed of a non-conductive material and disposed in an electrical apparatus which is charged with an insulating gas; a pair of electrodes disposed on the substrate in a spaced apart relationship; and a thin metal film disposed on the substrate so as to extend over the electrodes for electrical connection therebetween, the film being formed of a material which is highly reactive with decomposed components of the insulating gas which are produced when the electrical apparatus internally fails, the film changing its electrical resistance by reaction with the decomposed gas components.

According to another aspect of the present invention, there is provided a device for detecting internal faults in an insulating gas charged electrical apparatus comprising: an internal fault detection element disposed in the electrical apparatus charged with an insulating gas for detecting an internal fault in the electrical apparatus, the element changing its electrical resistance by reaction with decomposed components of the insulating gas which are produced when the electrical apparatus fails, the element having a pair of first and second electrodes; a current supplying means connected to the first electrode of the internal fault detection element for supplying current to the element; a photoelectric conversion means connected to the second electrode of the internal fault detection element for converting a change in the magnitude of the current output from the second electrode into an optical signal; and a signal processing means connected to the photoelectric conversion means for processing the optical signal supplied from the optical conversion means via an optical fiber.

BRIEF DESCRIPTION OF THE DRAWINGS

The present invention will be more readily apparent from the following detailed description of a few preferred embodiments thereof when taken in conjunction with the accompanying drawings in which.

DESCRIPTION OF THE PREFERRED EMBODIMENTS

The present invention will be described in detail with reference to a presently preferred embodiment thereof as illustrated in FIGS. 3A to 16.

Figure 3A:
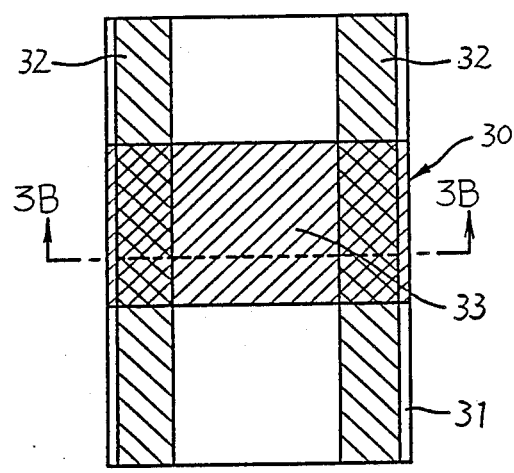
FIG. 3A is a plan view of an internal fault detection element for an insulating gas charged electrical apparatus in accordance with the present invention.
Figure 3B:
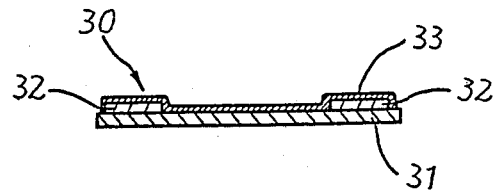
FIG. 3B is a cross-sectional view taken along the line 3B—3B of FIG. 3A.

FIG. 3A is a plan view of an internal fault detection element 30 in accordance with the present invention, while FIG. 3B is a cross-sectional view taken along the line 3B—3B of FIG. 3A. In FIGS. 3A and 3B, the internal fault detection element 30 comprises a substrate 31 formed of, for instance, sintered $Al_2O_3$; electrodes, such as gold (Au) electrodes 32, are disposed on both sides of the surface of the substrate 31; and a flat metal film, such as a thin silver (Ag) film 33 is disposed on the center of the substrate 31 and the surfaces of the Au electrodes 32 spanning the Au electrodes 32.

Figure 4A:
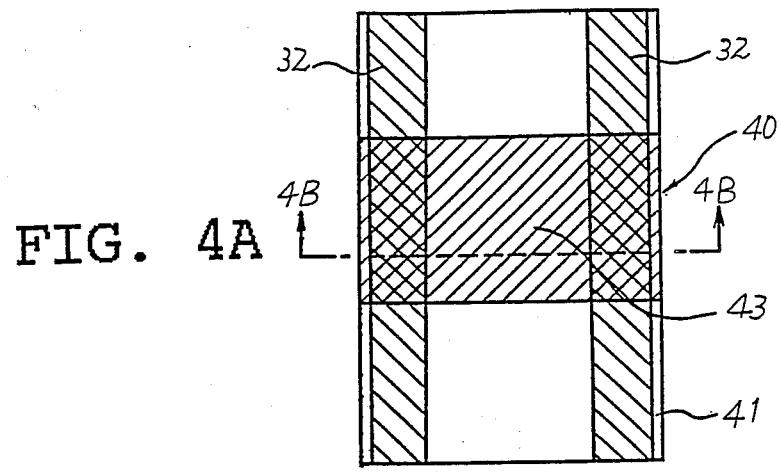
FIG. 4A is a plan view of another internal fault detection element in accordance with the present invention.
Figure 4B:
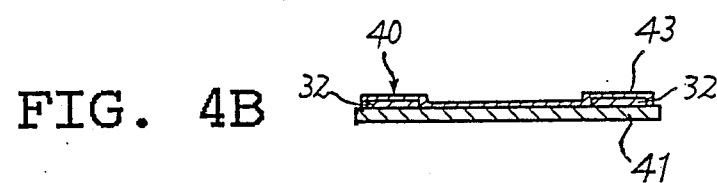
FIG. 4B is a cross-sectional view taken along the line 4B—4B of FIG. 4A.
Figure 4C:
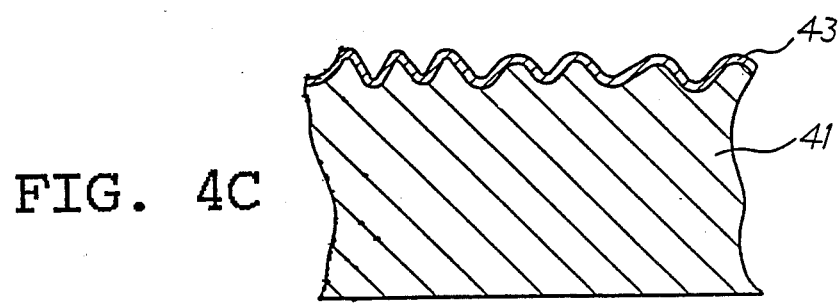
FIG. 4C is an enlarged cross-sectional view of another internal fault detection element as shown in FIGS. 4A and 4B.

4A is a plan view of another internal fault detection element 40 in accordance with the present invention, FIG. 4B is a cross-sectional view taken along the line 4B—4B of FIG. 4A, and FIG. 4C is an enlarged cross-sectional view of another internal fault detection element as shown in FIGS. 4A and 4B. In FIGS. 4A to 4C, the internal fault detection element 40 comprises a substrate 41 having a multiplicity of fine projections with a thickness of a few microns to several tens of microns and formed of, for instance, sintered $Al_2O_3$ obtained by sintering $Al_2O_3$ powder; electrodes, such as Au electrodes 32 are disposed on both sides of the surface of the substrate 41; and a thin metal film, e.g. a thin Ag film 43 is disposed on an exposed surface of the substrate 41 and the Au electrodes 32.

Figure 5:
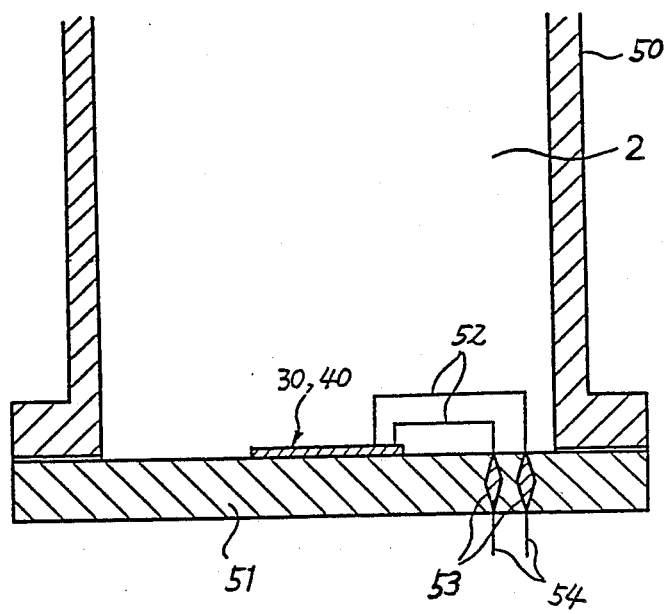
FIG. 5 is a partial cross-sectional view of a hermetic grounded metal vessel in which the internal fault detection element is provided.

The internal fault detection element 30 and 40 is provided on a flange 51 disposed in a hermetic grounded vessel 50 which is installed in an $SF_6$ charged electric apparatus (not shown), as shown, for instance, in FIG. 5, and is exposed to the $SF_6$ gas 2. Such an internal fault detection element 30 or 40 is electrically connected to an external circuit (not shown) via internal conductors 52, insulating sealed terminals 53 and external conductors 54.

In the internal fault detection element 30 or 40 having the above-described construction, if a fault such as a discharge or local heating occurs inside the $SF_6$ charged electrical apparatus in which the internal fault detection element 30 or 40 is installed, the $SF_6$ gas 2 is decomposed to generate an active decomposed $SF_6$ gas such as $SF_4$ or $SOF_2$. This decomposed $SF_6$ gas produces HF upon reacting with a trace amount of water contained in the $SF_6$ gas 2. The HF thus produced moves by natural convection and diffusion and reaches the surface of the internal fault detection device 30 or 40, where the HF reacts with the thin Ag film 33 or 43, thereby producing AgF as follows:

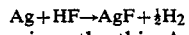

Thus, since the thin Ag film 33 or 43 is converted into a thin AgF film, the value of its resistance changes. Therefore, it is possible to detect a fault such as a discharge occurring inside the $SF_6$ charged electrical apparatus by monitoring this change in the resistance value through an external circuit (not shown) via the external conductors 54.

Figure 6:
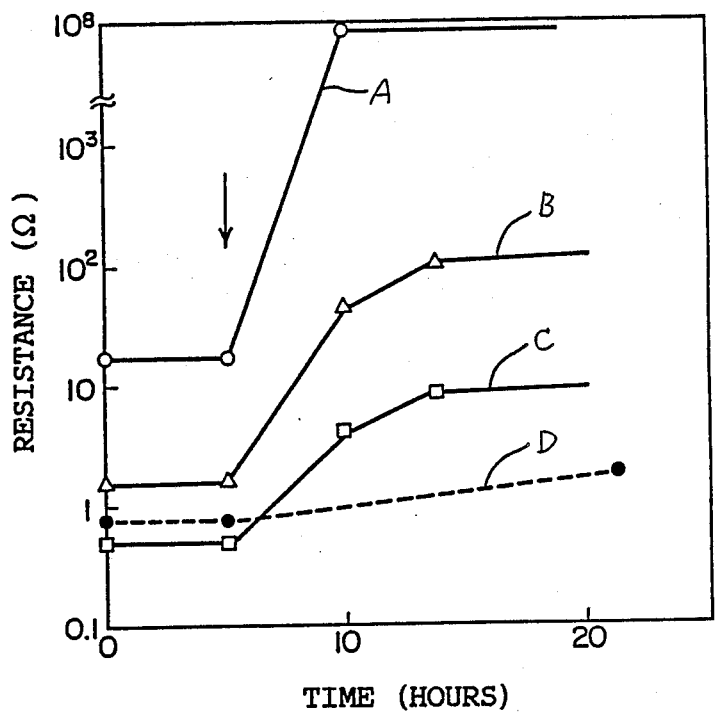
FIG. 6 is a diagram illustrating a change in a resistance value as a function of time when the internal fault detection element shown in FIG. 3A is exposed to SF.

FIG. 6 illustrates the change in resistance value as a function of time when the internal fault device 30 having the arrangement as shown in FIG. 3A or 3B is exposed to $SF_4$ (concentration: 1%) at room temperature under atmospheric pressure. In FIG. 6, curves A, B and C show the results of measurement of the internal fault detection element 30 in which thin Ag films 33 having thicknesses of 100Å, 300Å and 1000Å respectively were formed by, for instance, sputtering. Curve D shows, by way of comparison, the results of measurement of the conventional internal fault detection element 4 using the Al plate with a thickness of 5μm. The symbol ↓ represents the time when the $SF_4$ was introduced. As is apparent from FIG. 6, the internal fault detection element 30 in the three respective cases A, B, C exhibited greater response within a shorter time than that of the internal fault detection element 4, i.e., the comparative example D. Accordingly, at the time of the occurrence of a ground fault or the like in which the concentration of the decomposed $SF_6$ gas is high, it is possible to detect the internal fault with considerably higher sensitivity.

Figure 7:
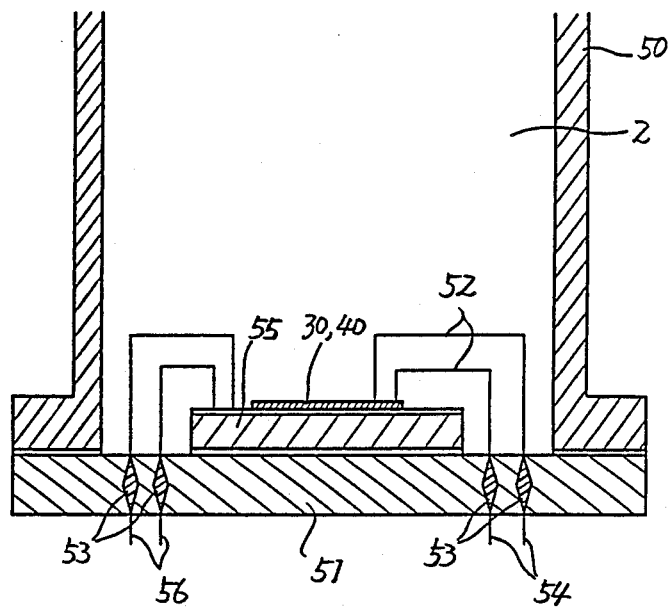
FIG. 7 is a partial cross-sectional view of the hermetic grounded metal vessel in which the internal fault detection element provided with an electronic refrigerating device is arranged.

FIG. 7 shows a partial cross-sectional view illustrating the hermetic grounded metal vessel 50 in which the internal fault detection element 30 or 40 is provided on a temperature control device, e.g. and electronic refrigeration device 55. In this drawing, reference numbers 2, 30, 40, 50, 51, 52, 53 and 54 denote the same or corresponding parts as those shown in FIG. 5. The internal fault detection element 30 or 40 is disposed on one surface of the electronic refrigeration device 55, and the other surface of the electronic refrigeration device 55 is disposed in such a manner as to be in contact with the inner wall surface of the hermetic grounded metal vessel 50. In addition, conductors 56 from a power source for heating or cooling the electronic refrigeration device 55 are connected to the electronic refrigeration device 55. The electronic refrigeration device 55 has a high-temperature side surface and a low-temperature side surface, and the internal fault detection element 30 or 40 can be heated by being disposed on the high-temperature side surface. When the internal fault detection device 30 or 40 is heated, the sensitivity of the thin Ag film 33 or 43 is further improved. Consequently, the detection at an early stage of such faults as partial discharge and local heating in the $SF_6$ charged electrical apparatus becomes even easier than in cases where the internal fault detection element 30 or 40 is not heated, even in low concentrations of decomposed $SF_6$ gas.

Figure 8:
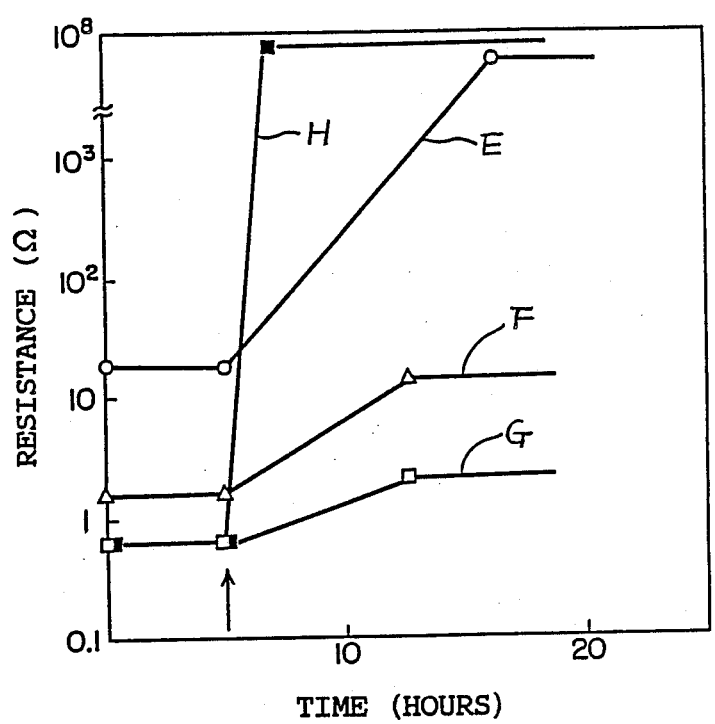
FIG. 8 is a diagram illustrating a change in a resistance value as a function of time when the internal fault detection element arranged as shown in FIG. 7 is exposed to $SF_4$.

FIG. 8 shows a change in resistance value as a function of time when the internal fault detection element 30 having the arrangement as shown in FIG. 7 is exposed to $SF_4$ (concentration: 100 ppm) under atmospheric pressure. In FIG. 8, curves E, F, and G show the results of measurement at room temperature of internal fault detection elements 30, in which thin Ag films 33 having thicknesses of 100Å, 300Å and 1000Å respectively were formed by, for instance, sputtering. Curve H shows the results measured when an electronic refrigeration device 55 having a thin Ag film 33 with a thickness of 1000Å formed thereon by, for instance, sputtering, was heated to 80°C. The symbol ↓ denotes the time when the $SF_4$ was introduced. As is apparent from FIG. 8, the sensitivity was not so high when the internal fault detection element 30 with a thin Ag film having a relatively large thickness of 1000Å was used. However, sufficient sensitivity was obtained when the internal fault detection element 30 was heated. Hence, it can be seen that even a decomposed $SF_6$ gas with a very low concentration can be detected. Furthermore, since the sensitivity becomes higher by heating the internal fault detection element 30, it is possible to use a thin Ag film 33 having a thickness of 1000Å or more.

In the above-described embodiment, Ag is used as the material for the thin metal film, however, any metal may be used if it is capable of forming a thin film of low resistance and produces fluorides, sulfides, etc. with reduced conductivity upon coming into contact with a decomposed $SF_6$ gas. In addition, in the above-described embodiment, a case has been described in which the high-temperature side of the electronic refrigeration device 55 was used as the device for controlling the temperature of the element 30 or 40. However, it is also possible to cool the internal fault detection element 30 or 40 by using the low-temperature side of the electronic refrigeration device 55. Namely, the internal fault detection element 30 or 40 is cooled below the dew point of the $SF_6$ gas 2 so as to condense or concentrate water and decomposed $SF_6$ gas on the surface and vicinity of the internal fault detection element 30 or 40. Then, the internal fault detection element 30 or 40 is again heated to a high temperature thereby accelerating the formation reaction of the above-mentioned fluoride. In this case, the concentrations of water and the decomposed $SF_6$ gas can be increased, therefore, making it possible to raise the sensitivity of the internal fault detection element 30 or 40. In the above, cooling and heating of the electronic refrigeration device 55 may be achieved by switching polarities of the electronic refrigeration device 55 to alternately change the high temperature side and low temperature side of the electronic refrigeration device 55.

In the above-mentioned embodiments, sintered $Al_2O_3$ was used as the substrate 31 or 41. However, another insulator having high thermal conductivity, such as sintered boron nitride (BN), which does not readily react with the decomposed gas and which has high adhesiveness with the Au electrode 32 and the Ag thin film 33 or 43, may also be used.

Figure 9:
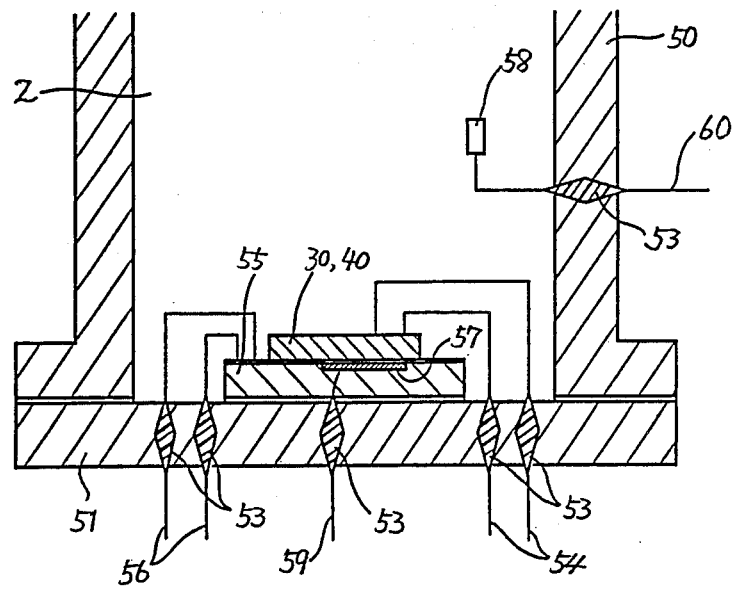
FIG. 9 is a partial cross-sectional view of the hermetic grounded metal vessel in which the internal fault detection element provided with a temperature sensor is arranged.

Moreover, as shown in FIG. 9, a temperature sensor 57 for the internal fault detection element 30 or 40 and a temperature sensor 58 for the $SF_6$ may be provided inside the hermetic grounded metal vessel 50. Outputs from these temperature sensors 57 and 58 may be connected to a temperature control circuit (not shown) via conductors 59 and 60 for a power source so as to maintain a set temperature in the vicinity of the internal fault detection element 30 or 40. In this case, it is possible to detect trace amounts of decomposed $SF_6$ gas on a stable basis without being affected by the ambient temperature.

Figure 10:
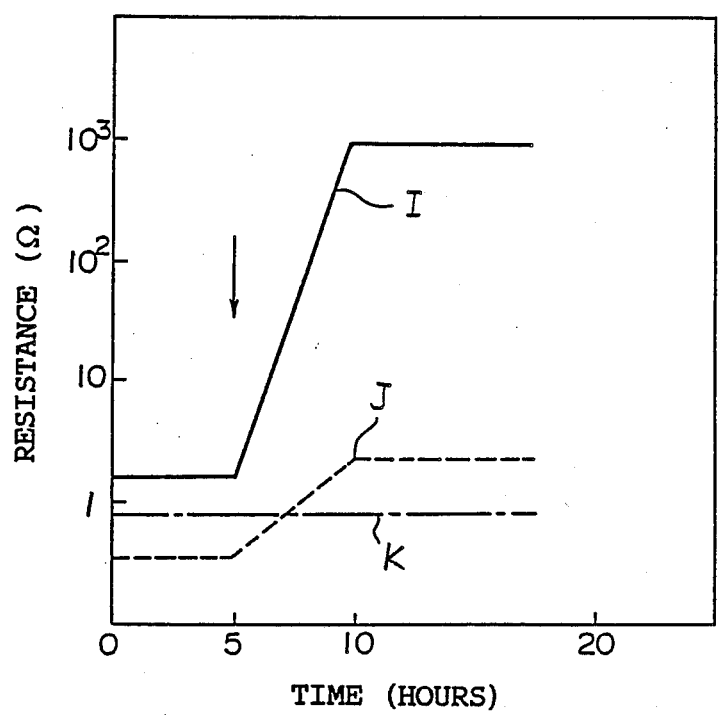
FIG. 10 is a diagram illustrating a change in a resistance value as a function of time when the internal fault detection element shown in FIG. 4A is exposed to $SF_4$.

FIG. 10 shows a change in resistance value as a function of time when the internal fault detection element 40 is exposed to $SF_6$ (atmospheric pressure) including $SF_4$ (concentration: 10 ppm). In FIG. 10, curve I shows the results of measurement of the internal fault detection element 40 in which a thin Ag film 43 having a thickness of 300Å was formed on the substrate 41 and which had on its surface fine projections with a thickness of several microns to several tens of microns formed by, for instance, sputtering. Curve J shows, by way of comparison, the results of measurement of an internal fault detection element 40 in which a thin Ag film 33 with a thickness of 300Å was formed on a substrate with a smooth surface by, for instance, sputtering. Curve K shows, by way of comparison, the results of measurement of a conventional fault detection element 4 using an Al plate with a thickness of 5μm. The temperature of each device was maintained at 80°C. The symbol ↓ denotes the time when the $SF_4$ was introduced. As is apparent from FIG. 10, the sensitivity of the conventional internal fault detection element 4 using the Al plate was very poor, but the internal fault detection element 40 having the thin Ag film 43 formed on the substrate 41 with the fine projections exhibited high-sensitivity response with respect $SF_4$, i.e, a decomposed $SF_6$ gas. This internal fault detection element 40 exhibited higher sensitivity than that of an internal fault detection device 30 having the thin Ag film 33 on a smooth substrate. This difference is considered to be the result of the following. Namely, if the thin Ag film 43 is formed on the substrate 41 with the fine projections by sputtering, the thickness of the film will not be uniform, and thickner portions and thinner portions of the thin Ag film 43 will be formed due to the uneven surface of the substrate 41. Consequently, the activity of reaction becomes higher in those thinner portions. In addition, the difference is also partly due to the larger surface area in the case of the substrate 41 having the fine projections. This is supported by the fact that in comparing the specific resistance of the devices using the two different substrates, the specific resistance is greater in the case where the thin Ag film 43 was formed on the substrate 41 having the fine projections.

Thus, by using an internal fault detection element 40 in which the thin Ag film 43 is formed on the substrate 41 having on its surface the fine projections with a thickness of several microns to several tens of microns, it is possible to detect promptly even internal faults in which the concentration of the decomposed $SF_6$ gas is low, such as when partial discharges and local heating occur in an electrical apparatus.

Figure 1:
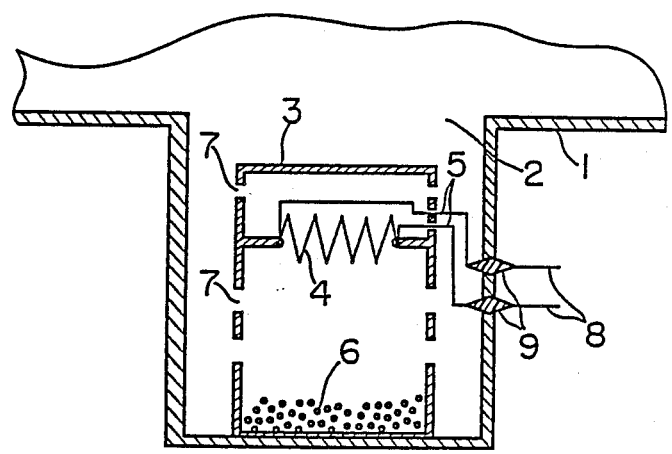
FIG. 1 is a partial cross-sectional view schematically illustrating a conventional device for detecting internal faults in an insulating gas charged electrical apparatus.
Figure 2:
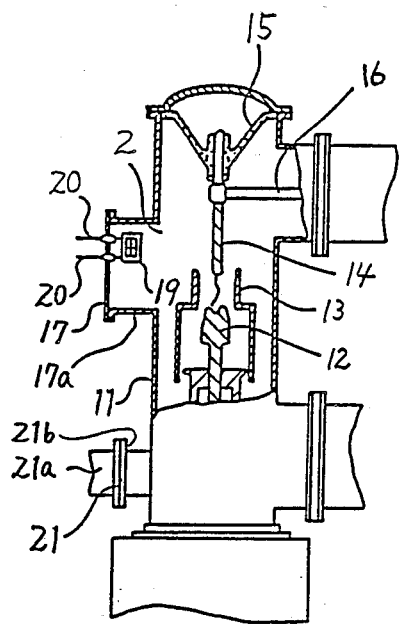
FIG. 2 is a cross-sectional view schematically illustrating another conventional device for detecting internal faults in an insulating gas charged electrical apparatus.
Figure 11:
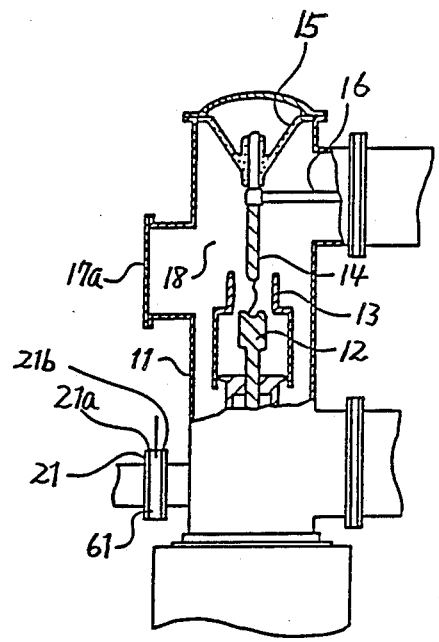
FIG. 11 is a cross-sectional view schematically illustrating an internal fault detection device provided with an internal fault detection element in accordance with the present invention.

FIG. 11 shows a cross-sectional view schematically illustrating a conventional internal fault detection apparatus as shown in FIG. 2, in which the internal fault detection element 30 or 40 in accordance with the present invention is incorporated. In FIG. 11, the same reference numerals as those of FIG. 2 denote the same or corresponding portions. An internal fault detector 61 is clamped between a gas pipe 21a and side pipe 21b on the gas pipe jointing portion 21. In FIG. 11, reference numeral 17a denotes a flange cover which merely serves to close an opening and is not provided with an internal fault detection portion.

Figure 12:
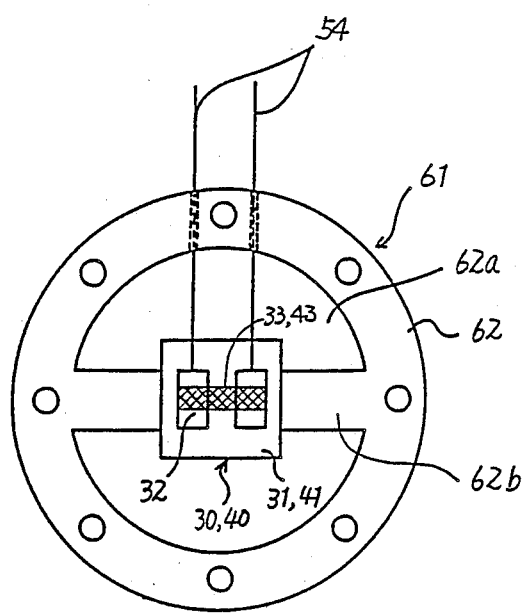
FIG. 12 is a plan view of an internal fault detection element installed in the internal fault detection device shown in FIG. 11.

The internal fault detector 61 is arranged as shown in FIG. 12. The internal fault detector 61 comprises a support frame 62 constituted by a planar member having a hollow portion 62a, and the internal fault detection element 30 or 40 fixed to a support crosspiece 62b provided in the hollow portion 62a. In addition, conductors 54 for outputting a signal output from the internal fault detection element 30 or 40 to the external circuit (not shown) hermetically pass through the support frame 62.

When the internal fault detector 61 is to be installed in an insulating gas charged electrical apparatus which is not provided with an internal fault detection apparatus, the gas pipe is removed at the gas pipe jointing portion 21, the internal fault detector 61 is inserted into the gap, and the gas pipe 21a and the side pipe 21b are then joined with the internal fault detector 61 therebetween.

After joining, the $SF_6$ gas 18 inside the hermetic vessel 11 and the thin Ag film 33 or 43 of the internal fault detection element 30 or 40 come into contact with each other. In this condition, if a discharge or local heating occurs, the SF$_6$ decomposes to form a decomposed SF$_6$ gas. This decomposed SF$_6$ gas reacts with the thin Ag film 33 or 43 thereby changing the electrical properties thereof. This change in the electrical properties is detected by electrodes 32, the detected signal representing the change is sent to the external circuit (not shown) via the conductors 54, and then an alarm is issued by a device (not shown).

In the above-described embodiment, a case has been described in which the internal fault detector 61 is installed in an insulating gas charged electrical apparatus not originally provided with an internal fault detection apparatus. However, the internal fault detector 61 can, of course, be provided in an electrical apparatus which is to be newly installed. In this case, the installation is carried out at the time of installing the piping.

Furthermore, as the flow of the gas is from an area of the gas that is subject to measurement towards the outside due to temperature rises caused by solar heating or the flow of current, if the sensitive surface of the internal fault detection element is disposed to face towards the electrical apparatus, the contact between the decomposed SF$_6$ gas and the sensitive surface thereof becomes even more reliable. Accordingly, an internal fault of the electrical apparatus can be detected even faster and more accurately.

Figure 13:
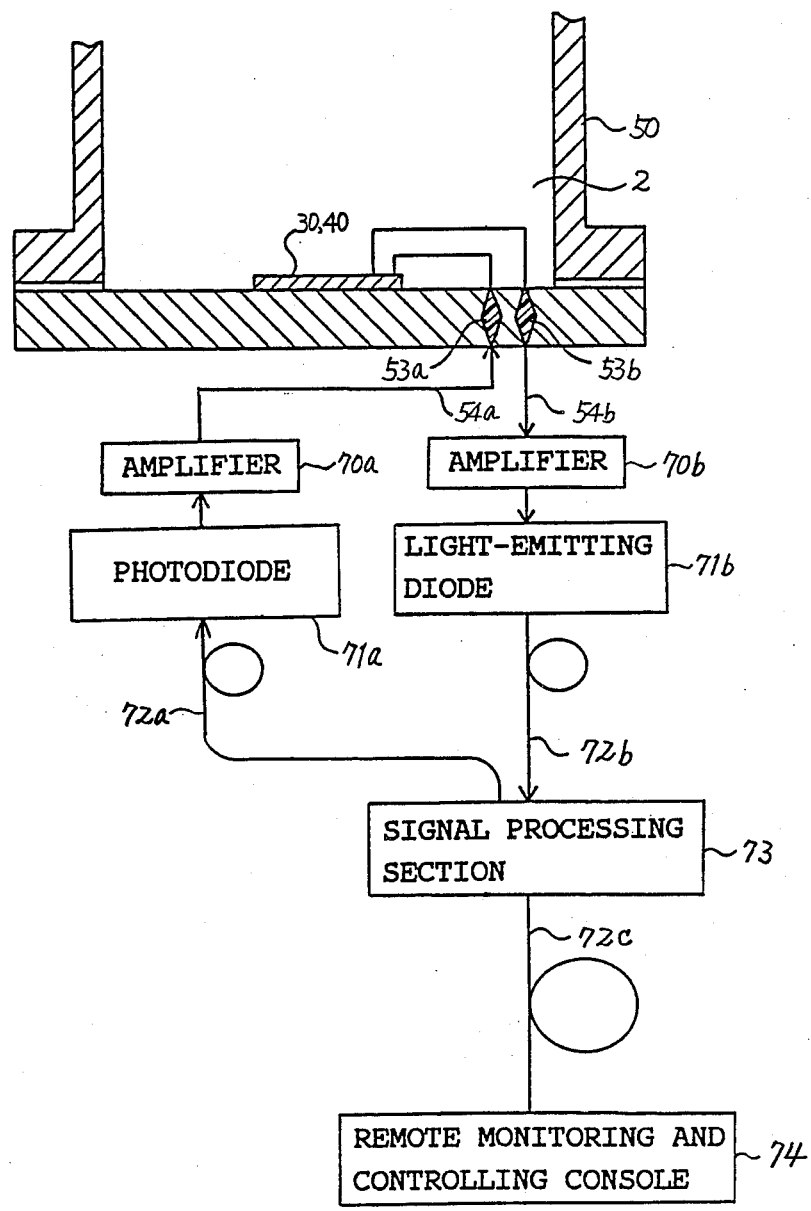
FIGS. 13 and 14 are block diagrams of an internal fault detection device in accordance with the present invention.

FIG. 13 is a block diagram of the internal fault detection device in accordance with the present invention, and the same or corresponding portions as those shown in FIG. 5 are denoted by the same reference numerals. In FIG. 13, one end of a conductor 54a is connected to the input side of the internal fault detection element 30 or 40, the other end thereof is connected to a photoelectric conversion section 71a, such as a photodiode, via an amplifier 70a. The other end of this photodiode 71a is connected to a signal processing section 73 by means of an optical fiber 72a. Similarly, one end of another conductor 54b is connected to the output side of the internal fault detection element 30 or 40, and the other end thereof is connected to a photoelectric conversion section 71b, such as a light-emitting diode, via an amplifier 70 b. The other end of the light-emitting diode 71b is connected to the signal processing section 73 by means of an optical fiber 72b. This signal processing section 73 is further connected to a remote monitoring and control console 74 by means of an optical fiber 72c. The photodiode 71a and the optical fiber 72a constitute current supplying means.

Figure 14:
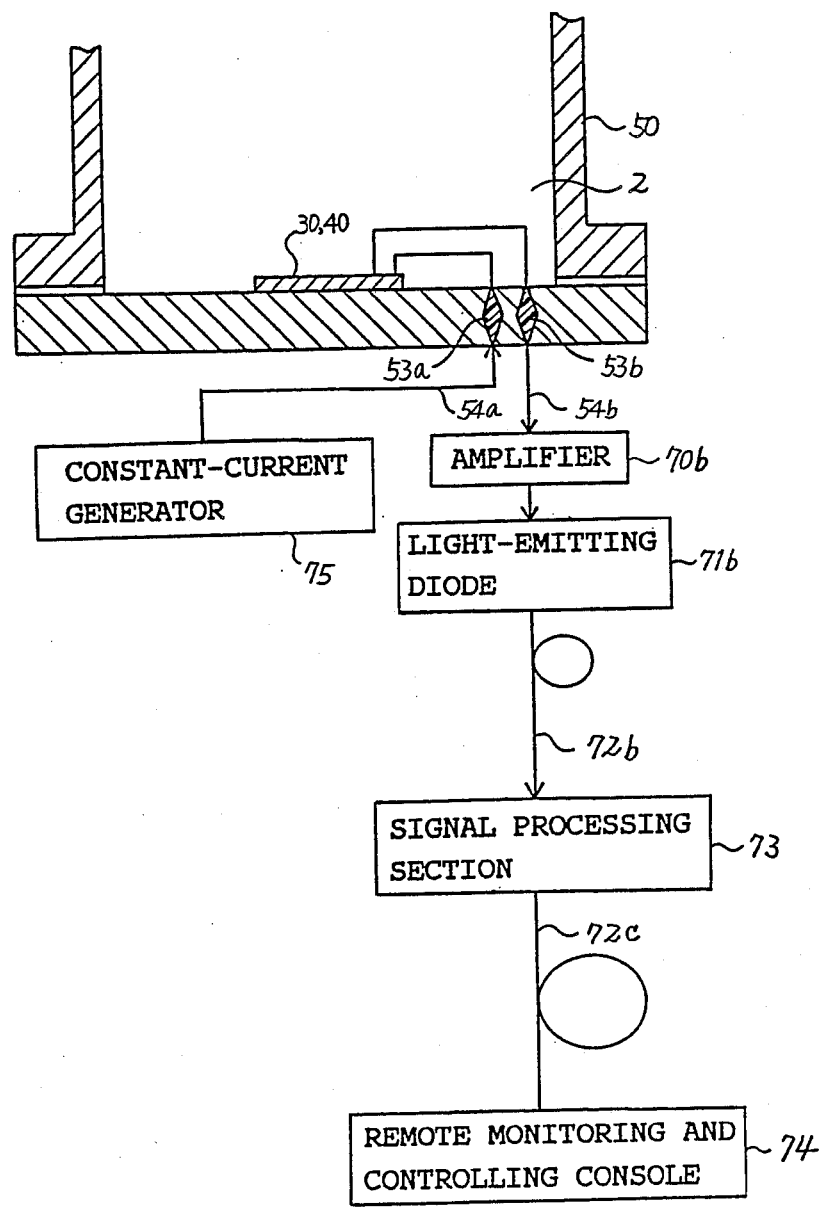

FIG. 14 is another block diagram of the internal fault detection device in accordance with the present invention, in which a constant-current generator 75 is used instead of the amplifiers and the photoelectric conversion section 71a as shown in FIG. 13.

Figure 15:
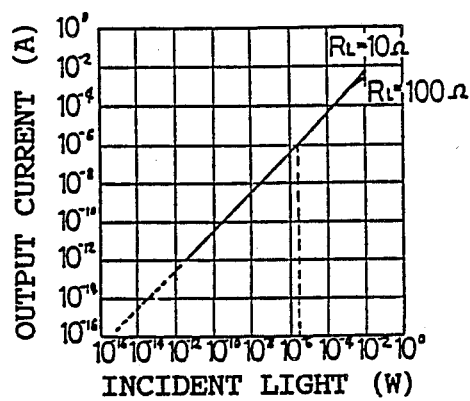
FIG. 15 is a diagram illustrating the relationships between the amount of incident light and output current according to one example of a photodiode used in an internal fault detection device as shown in FIGS. 13 and 14.
Figure 16:
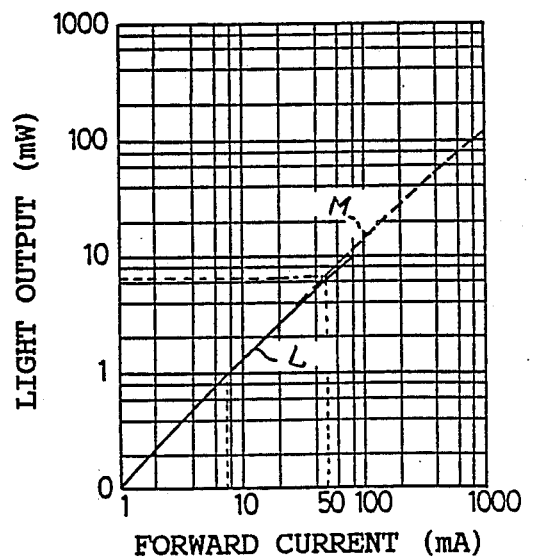
FIG. 16 is a diagram illustrating the relationships between current and output of light according to one example of a light-emitting diode used in an internal fault detection device as shown in FIGS. 13 and 14.

FIG. 15 is a graph illustrating the relationship between the amount of incident light and output current according to an example in which the photodiode 71a is used in the internal fault detection devices as shown in FIGS. 13 and 14. In FIG. 16, "L"and "M" depict direct current and pulse, respectively.

FIG. 16 is a graph illustrating the relationship between forward current and the output of light according to an example in which the light-emitting diode 71b is used in the internal fault detection devices as shown in FIGS. 13 and 14.

In the above-described device detecting internal faults in SF$_6$ charged electrical apparatus, an optical signal sent from the signal processing section 73 as shown in FIG. 13 is transmitted to the photodiode 71a via the optical fiber 72a, where the optical signal is converted into an electrical signal and is then amplified 70a to 1 mA or thereabout. If, for example, light of $6 \times 10^{-5}$W is made incident upon the photodiode 71a, an output current of $10^{-6}$A is obtained, as is apparent from FIG. 15. This output current is then amplified by the amplifier 70a to 1 mA. The 1 mA current thus obtained is led to the internal fault detection element 30 or 40 via the conductor 54a. If a fault occurs inside the hermetic grounded metal vessel 50 in the electrical apparatus, the SF$_6$ is decomposed and an active decomposed SF$_6$ gas such SF$_4$ and the like is produced. This decomposed SF$_6$ gas reacts with the amount of water existing in the SF$_6$ and produces HF and the like. The gas including HF converts good conductor Ag of the thin Ag film 33 or 43 of the internal fault detection element 30 or 40 into a poor conductor AgF, in the manner as described above. As a result of the change in the resistance of the thin Ag film 33 or 43, the current flowing through the conductor 54b connected to the output side of the internal fault detection element 30 or 40 changes. This changes of the electrical signal is amplified by the amplifier 70b, the amplified electrical signal is converted into an optical signal by the light-emitting diode 71b and is then detected. For instance, when the thin Ag film 33 with a thickness of 300Å, as shown by the curve B in FIG. 6, is used, the value of resistance, which is normally 1.5Ω, is changed to 10Ω when a fault occurs. At this time, only a 0.15 mA current flows through the conductor 54b although a 1 mA current would otherwise flow. If this current is amplified 50 times by the amplifier 70b, the current which would otherwise by 50 mA is changed to 7.5mA. This change in the current is subjected to photoelectric conversion by the light-emitting diode 71b and, on the basis of the relationship shown in FIG. 16, its optical output changes from 6.5 mW to 1 mW. The optical signal thus obtained is transmitted to the signal processing section 73 through the optical fiber 72b, where the optical signal undergoes signal processing. Furthermore, if the optical signal is sent to the remote monitoring control console 74 using the optical fiber 72c, an internal fault occuring in an electrical apparatus can be remotely monitored.

In addition, if the constant-current generator 75 is used as shown in FIG. 14, a current generated by the generator 75 which produces a constant current of, for instance, 1 mA, is supplied to the internal fault detection element 30 or 40. The subsequent change in the signal takes place in the same manner as the process as shown in FIG. 13.

Further, according to another experiment performed at the same time as the experiment using the thin Ag film 33 according to FIG. 6, wherein a thin Ag film having a sectional area of $6 \times 10^{-4}$mm$^2$($300 \times 10^{-7}$mm $\times$ 20 mm) with a thickness of 300Å and an Al$_2$O$_3$ substrate (40 mm $\times$ 20 mm) was used, no appreciable thermal effect was observed through the application of a 500A/mm$^2$current.

While a few presently preferred embodiments of the present invention have been shown and described herein, it will be apparent to those skilled in the art that various changes and/or modifications thereof can be made without departing from the spirit and scope of the invention as defined in the appended claims.

What is claimed is:

1. An element for detecting internal faults in an insulating gas charged electrical apparatus comprising:

a substrate formed of a non-conductive material;
a pair of electrodes disposed on said substrate in a spaced apart relationship; and
a thin metal film disposed on said substrate extending over said electrodes and electrically connecting them, said metal film reacting with decomposition components of a fluorine compound insulating gas, produced when electrical apparatus charged with said insulating gas fails, to form metallic fluorine compounds, thereby increasing the electrical resistance of said film.

2. An element for detecting internal faults as claimed in claim 1 wherein said substrate is formed of sintered $Al_2O_3$.

3. An element for detecting internal faults as claimed in claim 1 wherein said substrate is formed of sintered BN.

4. An element for detecting internal faults as claimed in claim 1 wherein said substrate is disposed on a heating element.

5. An element for detecting internal faults as claimed in claim 4 wherein said heating element is a temperature control device.

6. An element for detecting internal faults as claimed in claim 1 wherein said substrate is disposed on an electrical refrigeration element.

7. An element for detecting internal faults as claimed in claim 6 wherein said electronic refrigeration element is a temperature control device.

8. An element for detecting internal faults as claimed in claim 5 wherein said temperature control device is disposed in contact with an electrical apparatus.

9. An element for detecting internal faults as claimed in claim 5 wherein said temperature control device is an electronic refrigeration device.

10. An element for detecting internal faults as claimed in claim 1 wherein said electrodes are gold electrodes.

11. An element for detecting internal faults as claimed in claim 1 wherein said thin metal film is a thin silver film.

12. An element for detecting internal faults as claimed in claim 1 wherein the thickness of said thin metal film is 1000Å or less.

13. An element for detecting internal faults as claimed in claim 1 wherein said thin metal film is formed of sputtered metal.

14. An element for detecting internal faults as claimed in claim 1 wherein said substrate has fine projections formed on its surface.

15. An element for detecting internal faults as claimed in claim 14 wherein the thickness of said fine projections on said substrate surface is several microns to several tens of microns.

16. An element for detecting internal faults as claimed in claim 14 wherein the thickness of said thin metal film which covers said exposed surface of said substrate having fine projections is in the range of 200Å to 400Å.

17. An element for detecting internal faults as claimed in claim 1 wherein said element is disposed on a planar support having at least one central opening for installation at a gas pipe joint.

18. An element for detecting internal faults as claimed in claim 17 including airtight electrical feedthroughs in said support and electrical leads connected to said element and extending through said support and feedthroughs to the outside of said support.

19. An element for detecting internal faults as claimed in claim 1 wherein said insulating gas is $SF_6$.

20. A device for detecting internal faults in an insulating gas charged electrical apparatus comprising:
an internal fault detection element for placement in an electrical apparatus charged with a fluorine compound insulating gas and for detecting internal faults in said electrical apparatus by reacting with decomposed components of said insulating gas which are produced when said electrical apparatus fails to form metallic fluorine compounds and thereby increase in electrical resistance, said element having a substrate formed of a non-conductive material, a pair of first and second electrodes disposed on said substrate in a spaced apart relationship, and a thin metal film disposed on said substrate extending over said electrodes and electrically interconnecting them;
current supplying means connected to one of said electrodes of said internal fault detection element for supplying current to said element;
photoelectric conversion means connected to the other of said electrodes of said internal fault detection element for converting a change in the magnitude of the current flowing through said element into an optical signal; and
signal processing means connected to said photoelectric conversion means for processing the optical signal.

21. A device for detecting internal faults as claimed in claim 20 wherein said current supplying means comprises a second photoelectric conversion means connected to said signal processing section for converting a second optical signal sent from said signal processing section fiber into a current which is supplied to said 22. A device for detecting internal faults as claimed in claim 21 wherein said second photoelectric conversion means is a photodiode.

23. A device for detecting internal faults as claimed in claim 20 wherein said current supplying means is a constant-current generator for supplying a predetermined constant current.

24. A device for detecting internal faults as claimed in claim 20 wherein said photoelectric conversion section is a light-emitting diode.

25. A device for detecting internal faults as claimed in claim 20 including an optical fiber cable and wherein said signal processing section is connected to a remote monitoring console by said optical fiber cable.

26. A device for detecting internal faults as claimed in claim 21 wherein said insulating gas is $SF_6$.

* * * * *